United States Patent [19]
Campbell et al.

[11] Patent Number: 6,093,184
[45] Date of Patent: *Jul. 25, 2000

[54] FLEXIBLE VALVE ROTATOR

[75] Inventors: Louis A. Campbell; Joseph A. Sauter, both of Austin; Thomas W. Lytle, IV, Round Rock, all of Tex.

[73] Assignee: Sulzer Carbomedics Inc., Austin, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/850,412

[22] Filed: May 2, 1997

Related U.S. Application Data

[63] Continuation-in-part of application No. 08/409,331, Mar. 23, 1995, abandoned.

[51] Int. Cl.[7] .................................................. A61B 17/00
[52] U.S. Cl. ...................................... 606/1; 623/2; 606/99
[58] Field of Search ............................ 623/2; 606/1, 99, 606/108, 113

[56] References Cited

U.S. PATENT DOCUMENTS

| | | | |
|---|---|---|---|
| 3,628,535 | 12/1971 | Ostrowsky et al. | |
| 4,655,218 | 4/1987 | Kulik et al. | 128/321 |
| 4,683,883 | 8/1987 | Martin et al. | 128/303 |
| 4,982,727 | 1/1991 | Sato | 128/4 |
| 5,236,450 | 8/1993 | Scott | 623/2 |
| 5,403,305 | 4/1995 | Sauter et al. | 606/1 X |
| 5,409,478 | 4/1995 | Gerry et al. | 606/1 |
| 5,443,502 | 8/1995 | Caudillo et al. | 623/2 |
| 5,531,785 | 7/1996 | Love et al. | 623/2 |
| 5,582,607 | 12/1996 | Lackman | 606/1 |
| 5,609,601 | 3/1997 | Kolesa et al. | 606/170 |
| 5,788,689 | 8/1998 | Allan et al. | 606/1 |
| 5,860,992 | 1/1999 | Daniel et al. | 606/144 X |

OTHER PUBLICATIONS

Informational Brochure:Snowden Pencer, Diamond–Flex Surgical Instruments.
Informational Brochure: S.S. White Technologies Inc., Ready–Flex Standard Flexible Shafts and Ratio Drives.
Duerig, T.W., et al. Superlelastic Nitinol for Medical Devices, Medical Plastics and Biomaterials, Mar./Apr. 1997, pp. 30–43.
Internet Article: Hodgson, D.E., et al. Shape Memory Alloys, Shape Memory Allocations, Inc., pp. 1–11.
Internet Article: Applications of Shape Memory and Superelastic Alloys, Shape Memory Applications, Inc., pp. 1–2.
Internet Article: NITI Technical Information, Shape Memory Applications, Inc., pp. 1–2.

(List continued on next page.)

*Primary Examiner*—Cary O'Connor
*Assistant Examiner*—Ryan Carter
*Attorney, Agent, or Firm*—Timothy L. Scott; Philip S. Lyren; Kenneth S. Barrow

[57] ABSTRACT

A heart valve prosthesis rotator having a flexible drive for flexibly turning a heart valve. One embodiment has a shaft constructed from elastically deformable metal alloy such as super elastic nickel-titanium alloy. Another embodiment has a shaft constructed of surgical tubing. Yet another embodiment also has an annealed stainless steel shaft which can be bent by the surgeon interoperatively. The shaft will retain its shape after bending. Surrounding the shaft is a drive coil which connects a rotator head at a proximal end of the shaft to a drive knob at a distal end of the shaft and adjacent a handle. By turning the drive knob, a surgeon can turn the rotator head, thus orienting the prosthetic heart valve. Torsional motion is carried along the path defined by the bendable shaft so that the rotator head can be turned without displacing the handle of the heart valve rotator.

8 Claims, 6 Drawing Sheets

OTHER PUBLICATIONS

Internet Article: Glossary of Niti Terminology, NiTi Smark Sheet, pp. 1–2.
Internet Article: Introduction to Shape Memory and Super-elasticity, NiTi Smark Sheet, pp. 1–2.
Internet Article: Selected Properties of NITI, NiTi Smart Sheet, pp. 1–2.
Internet Article: Two–Way Memory, NiTi Smart Sheet, pp. 1–2.
Internet Article: Biocompatibility of NITI, NiTi Smart Sheet, pp. 1–2.
Internet Article: Setting Shapes in NITI, NiTi Smart Sheet, p. 1.
Internet Article: Making Shape Memory Springs, NiTi Smart Sheet, pp. 1–2
Internet Article: NITI Actuator Wire Properties, NiTi Smart Sheet, pp 1–2.
Internet Article: Comparison of Properties of NITI and Stainless Steel, NiTi Smart Sheet, p. 1.
Internet Article: Approximate Surface Strains in Wire, Ribbon and Sheet, NiTi Smart Sheet, pp. 1–2.
Internet Article: Measuring Transformation Temperatures in NITI Alloys, NiTi Smart Sheet, pp. 1–3.
Internet Article: Transformation Temperature Hysteresis in NITI Alloys, NiTi Smart Sheet, pp. 1–2.
Internet Article: Selected NITI References, pp. 1–3.
Internet Article: SMA, Inc. Products and Services, Shape Memory Applications, Inc., pp. 1–4.
Internet Article: Lin, Richard, Shape Memory Alloys and Their Applications. pp. 1–6.
Internet Article: MedicalGuidewires, p. 1.
Internet Article: MedicalGuidepins, p. 1.
Internet Article: BendableSurgical Tools, p. 1.

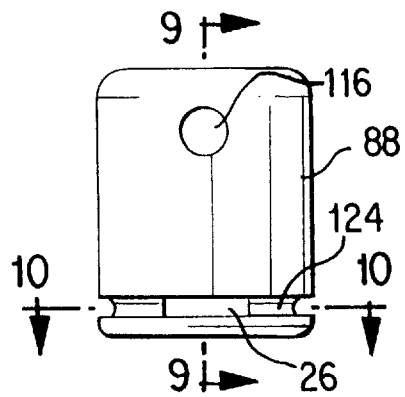
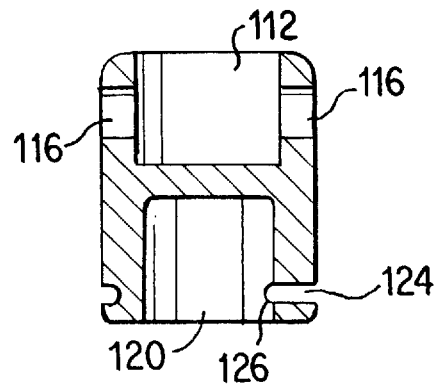
FIG. 8　　　　　FIG. 9
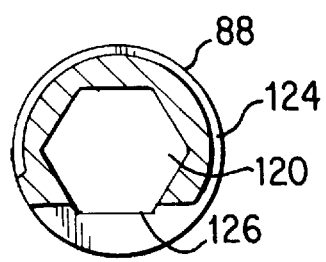
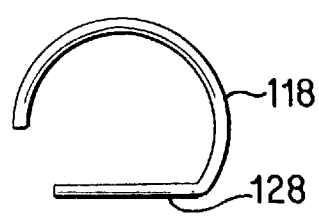
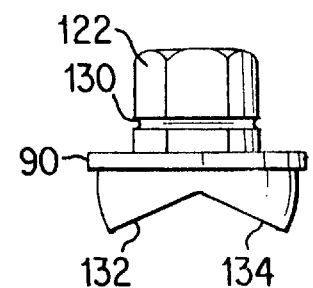
FIG. 10　　FIG. 11　　FIG. 12
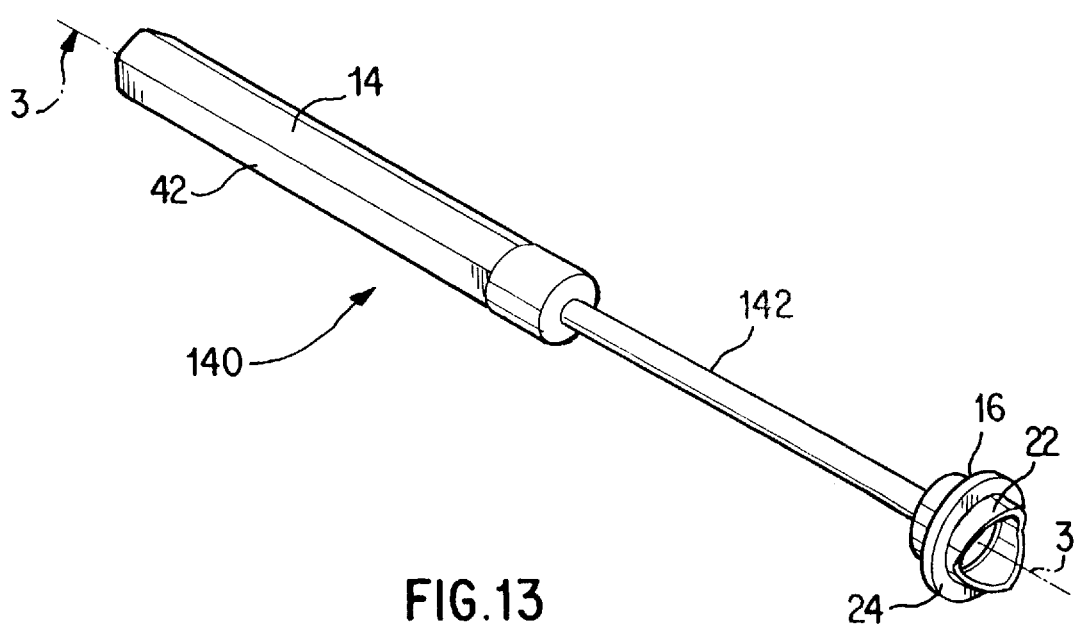
FIG. 13

FLEXIBLE VALVE ROTATOR

This is a continuation-in-part of application Ser. No. 08/409,331 filed Mar. 23, 1995, now abandoned.

BACKGROUND OF OUR INVENTION

1. Field of our Invention

Our invention pertains to apparatus for manipulating mechanical heart valve prostheses and in particular to a heart valve prosthesis rotator having a flexible drive shaft.

2. Description of Related Art

Mechanical Heart Valve Prosthesis include ball valves and valves having one, two or more rigid leaflets. One popular valve design for a mechanical heart valve prosthesis includes an annular valve body in which a pair of opposed leaflet occluders are pivotally mounted. The occluders are movable between a closed, mated position, blocking blood flow in an upstream direction and minimizing regurgitation, and an open position, allowing blood flow in a downstream direction. The annular valve body is surrounded by a sewing ring which permits the surgeon to suture the valve in place at the site of an excised valve.

When a valve is placed within the heart, it must be accurately oriented to maximize its function. Particularly in mechanical heart valves, the orientation of the leaflets is critical since their opening and closing pathways may otherwise impinge on the surrounding cardiac walls, the walls of arteries within which the valve is placed, or the residual valvular structures including the tendeae chordae and papillary muscles. This difficulty becomes particularly acute when in the placement of a heart valve in the position of the mitral valve in the heart. When replacing this valve, a surgeon will frequently expose the posterior side of the patient's heart and enter the heart through the wall of the left atrium and sometimes through the right atrium. It is desirable to place the valve accurately within the cramped confines of the heart while leaving room for the surgeon to sew the valve in place.

To aid in the rotation of the heart valve within a sewing ring, heart valve prosthesis rotators have been proposed heretofore. Some of these rotators have bendable metal shafts which can be bent by the surgeon interoperatively, but which will retain their bent shape, requiring significant space for proper manipulation of a heart valve engaged by the rotator. The shafts of some of these rotators are constructed of a shape-memory alloy, which construction allows the shaft to recover its original straight shape upon sterilization. The term "shape-memory alloys" refers to that group of metallic materials that demonstrate the ability to return to same previously defined shape and size when subjected to the appropriate thermal procedure. These materials can be plastically deformed at some relatively low temperature, and upon exposure to higher temperatures, will return their shape prior to the deformation. Rotators containing shape-memory alloy shafts can be easily positioned by bending the shaft to the desired orientation. To return the shaft to its original shape, the shaft is heated (i.e., during the sterilization process) to a temperature above the alloy's transformation temperature.

With the increased use of less invasive cardiac surgical procedures a rotator is needed that can turn a heart valve within a very limited space. To accomplish this, a rotator must have both flexibility and torqueability (i.e. kink resistance). The rotator must have the ability to absorb large amounts of strain energy and release it as the applied strain is released.

SUMMARY OF THE INVENTION

We have invented a heart valve prosthesis rotator which has a flexible drive shaft. In use the drive shaft can be bent to a desired direction but will transmit torque to a heart valve rotator head, orienting a prosthetic heart valve mounted thereon. Moreover, the shaft will return to its original shape after force is removed. The shaft may be constructed of material such as super-elastic nickel-titanium alloy, which rotator is easily sterilized for re-use. The elastic shaft may also be constructed of a lower cost polymeric material such as surgical tubing, which is better suited for single-use applications.

We have also invented a heart valve prothesis rotator which also has an annealed stainless steel shaft which can be bent by the surgeon interoperatively. The shaft will retain its shape after bending. Surrounding the shaft we have provided a drive coil which connects a rotator head at a proximal end of the shaft to a drive knob at a distal end of the shaft and adjacent a handle. By turning the drive knob, a surgeon can turn the rotator head, thus orienting the prosthetic heart valve. Torsional motion is carried along the path defined by the bendable shaft so that the rotator head can be turned without displacing the handle of the heart valve rotator.

With the foregoing in mind, it is a principal object of our invention to provide a heart valve prosthesis rotator with elastic shaft that can bend to a desired shape and at the same time supply torque to the heart valve rotator head through an axial rotation of the shaft.

It is also an object of our invention to provide a heart valve prosthesis rotator with a bendable shaft for guiding said drive coil.

These and other objects and features of our invention will be apparent to those skilled in the art from the following detailed description of our preferred embodiment taken with reference to the accompanying drawings.

BRIEF DESCRIPTION OF THE DRAWINGS

FIG. 8 is a plan view of a proximal connector of the embodiment of FIG. 4.

FIG. 9 is a through section in plan view of the connector of FIG. 8, taken along line 9—9 of FIG. 8.

FIG. 10 is a through section in top view of the proximal connector of FIG. 8, taken along line 10—10 of FIG. 8.

FIG. 11 is a plan view of a D-ring for use with the connector of FIG. 8.

FIG. 12 is a plan view of a detachable rotator head of the embodiment of FIG. 4.

FIG. 13 is a general perspective view of a third embodiment of our invention.

DETAILED DESCRIPTION OF OUR PREFERRED EMBODIMENT

Figure 1:
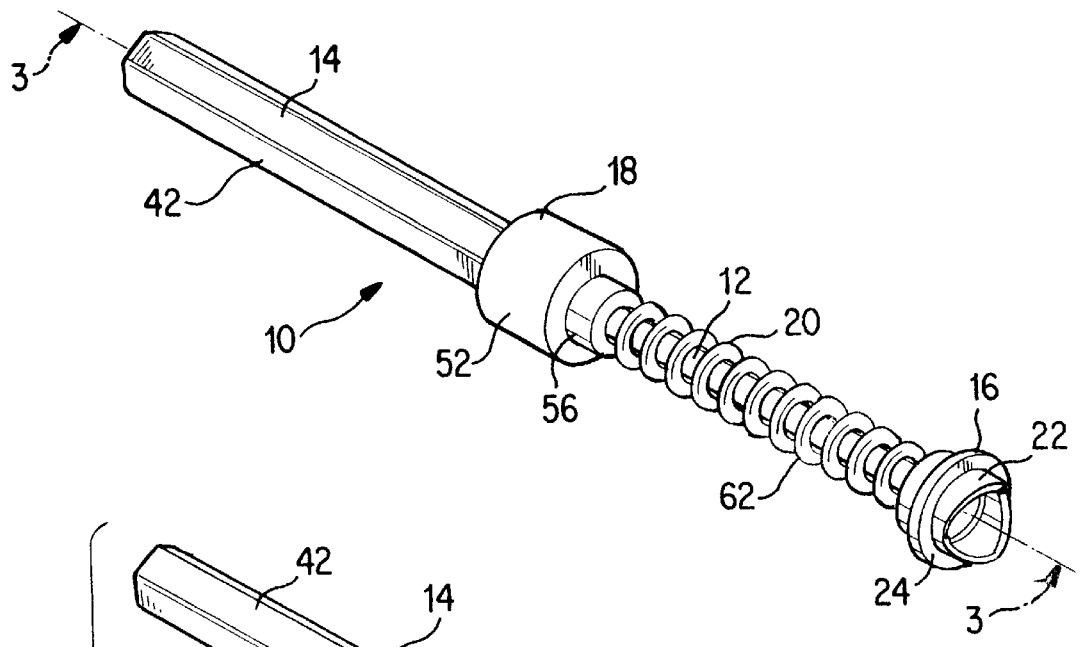
FIG. 1 is a perspective view of a heart valve rotator according to our invention.

Referring now to the drawings, a heart valve prosthesis rotator, generally designated 10, is shown in perspective view in FIG. 1. The rotator 10 comprises an annealed stainless steel shaft 12 with a metal or plastic handle 14 at a distal end thereof. "Proximal" denotes a part of an apparatus which is relatively close to the heart when in use, as is customary in cardiovascular surgery. "Distal" denotes a part remote from the heart and, consequently, near the physician. At a proximal end of the shaft 12 there is a rotator head 16. At a proximal end of the handle 14, there is a drive knob 18. A drive coil 20 connects the drive knob 18 to the rotator head 16.

Mechanical heart valves generally comprise an annular body containing one, two or more leaflets or occluders. Leaflets move from a closed position impeding the flow of blood to an open position, permitting flow of blood. In our preferred embodiment, the rotator head 16 is described with a configuration for a bileaflet mechanical heart valve for use in the mitral position in the heart. Those skilled in the art, however, will recognized that rotator heads may be constructed for single leaflet valves as well as for trileaflet or multiple leaflet valves and for the mitral or atrial positions without departing from the spirit or teachings of our invention.

Figure 2:
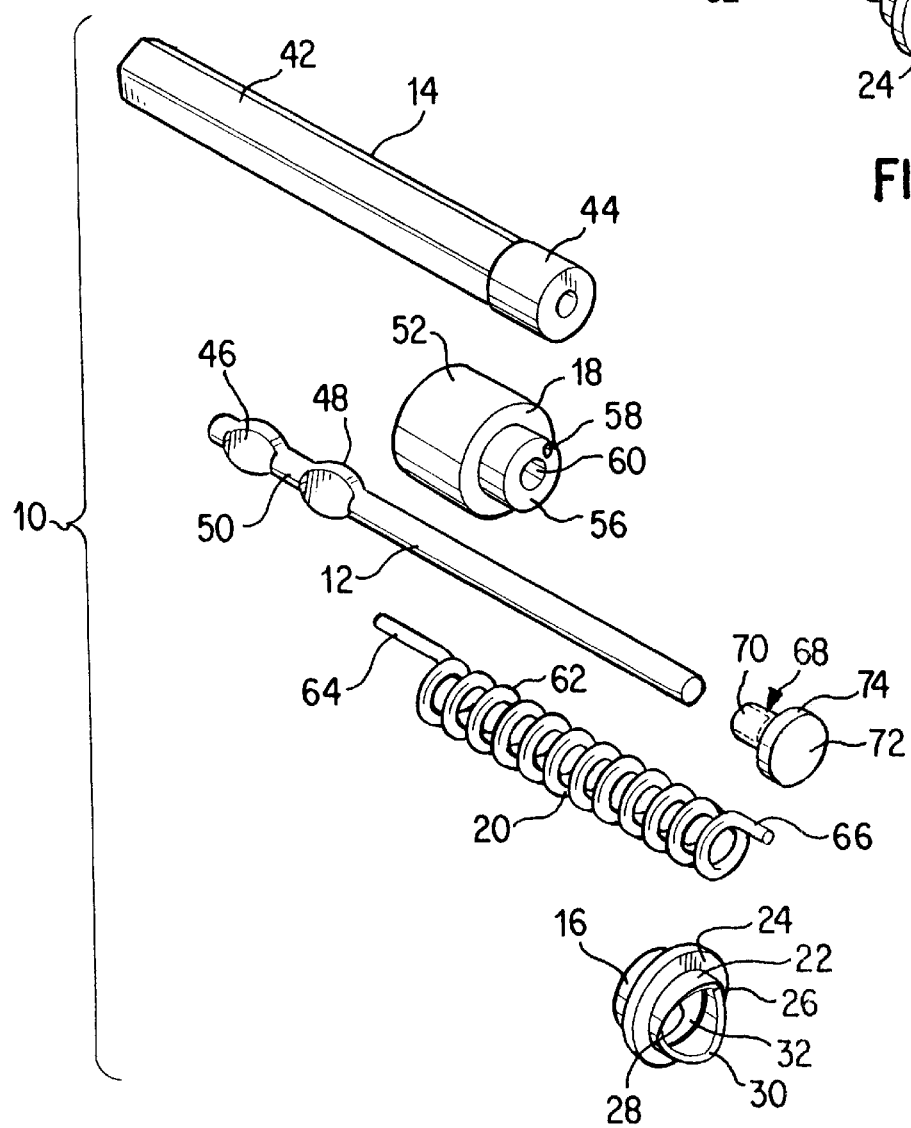
FIG. 2 is an exploded perspective view of the heart valve rotator of FIG. 1.
Figure 3:
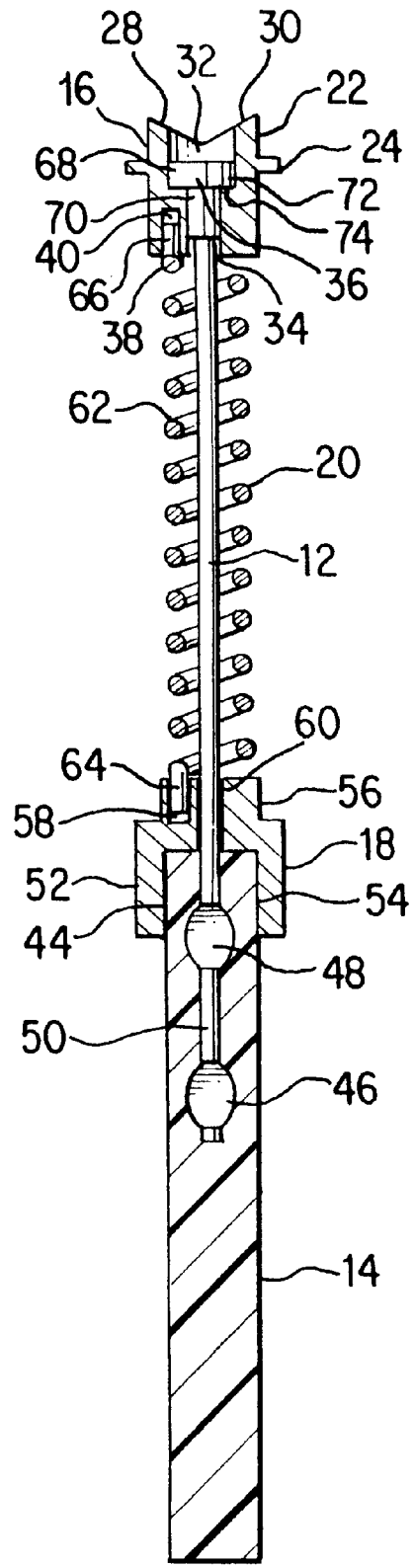
FIG. 3 is a through section of the heart valve rotator of FIG. 1, taken along line 3—3 of FIG. 1.
Figure 4:
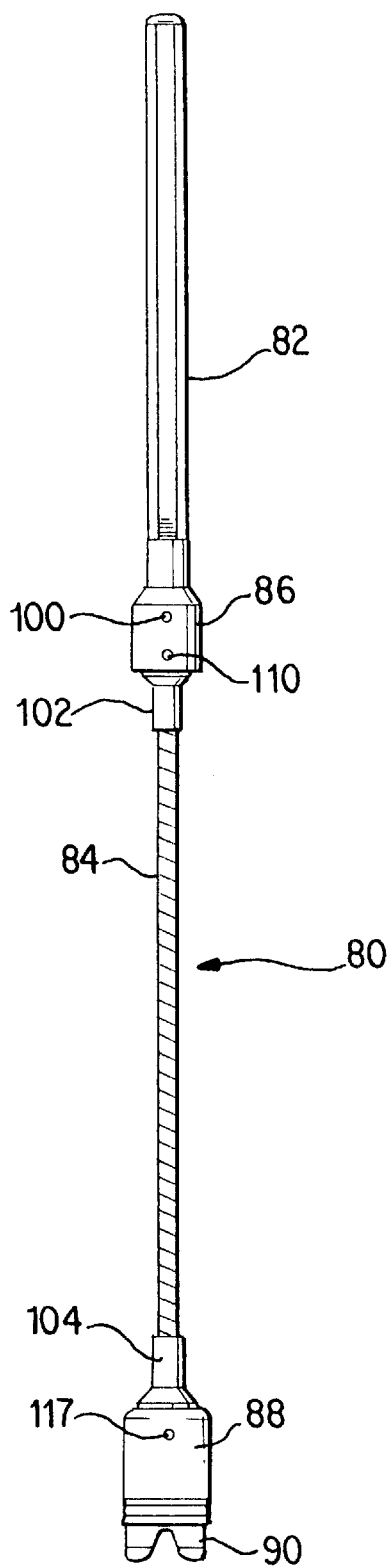
FIG. 4 is a plan view of a second embodiment of our invention.

The rotator head 16 is shown in perspective view both in FIGS. 1 and 2 and in through section in FIG. 3. The rotator head 16 comprises a generally cylindrical body 22 having a annular lip 24. The annular lip 24 will engage the annular body of a heart valve. At a proximal end 26 of the cylindrical body 22 are surfaces 28, 30 for engaging the leaflets of a bileaflet heart valve. The two surfaces 28, 30 meet at an obtuse included angle in configurations for use with a bileaflet mitral heart valve. For a bileaflet atrial valve, of course, the angle at which the two surfaces meet would be greater than 180 degrees, that is, the most proximal part of the heart valve rotator head would be the points where the two surfaces 28, 30 meet. Other configurations would be adopted for single leaflet or trileaflet valves, the configuration of these surfaces being dictated by the configuration of the valve to be manipulated.

There is a proximal bore 32 extending from the proximal end 26 of the rotator head into the rotator head 16. Coaxially with the proximal bore 32 there is a distal bore 34, which has a smaller diameter than the proximal bore. These two bores 32, 34 meet within the rotator head 16, forming a circumferential edge 36. At a distal end 38 of the rotator head 16, there is a offset stopped bore 40 for engaging the drive coil 20, as will be more particularly described hereafter.

In our preferred embodiment, the handle 14 is formed of plastic and can be molded around the bendable shaft 12 so that the handle 14 and the shaft 12 are securely attached to one another. The handle 14 has a distal grip 42 with suitable features to provide a secure grip for the surgeon. We have illustrated a hexagonal shape for the grip 42, but other suitable shapes could also be chosen. Proximally on the handle 14, there is a cylindrical section 44 about which the drive knob 18 turns. The shaft 12, preferably composed of annealed stainless steel, has two flats 46, 48 provided at a distal end 50 thereof. Preferably, the handle 14 is molded around the shaft 12 with the flats 46, 48 within the handle. This provides a secure connection between the shaft 12 and the handle 14.

The drive knob 18 comprises a collar 52 which has an internal cavity 54, sized to fit over the cylindrical section 44 of the handle 14. Proximally from the collar 52 is a cylindrical neck 56 having an offset stopped bore 58 which engages the drive coil 20, as will be more fully described below. A central through bore 60 extends through the neck 56 into the cavity 54. The shaft 12 passes through this bore 60 and the drive knob 18 can, therefore, be rotated about the cylindrical section 44 of the handle 14 and the shaft 12. The drive coil 20 essentially comprises a coiled spring 62 which fits around the shaft 12. At each end of the spring 62 there is a tang. A distal tang 64 fits into the stopped bore 58 of the drive knob 18. A proximal tang 66 fits into the stopped bore 40 in the rotator head 16. Thus, turning the drive knob 18 will impart torsional motion through the drive coil 12 to the rotator head 16 without significant motion of the handle 14. This is true even if the shaft 12 has been bent into a nonlinear shape. The drive coil 12 will be able to follow that shape and still transfer the torsional motion to the rotator head.

The drive knob 18, drive coil 20 and rotator head 16 are held on the handle 14 and shaft 12 by a retainer 68. The retainer 68 comprises a cylinder 70 with an internal bore which fits over the proximal end of the shaft 12. A press fit is used to attach the retainer to the end of the shaft 12. Of course, other methods of securing the retainer 68 could also be selected, such as threads or adhesive. A cap 72 forms a circumferential lip 74 which engages the edge 36 formed by the intersection of the proximal bore 32 and the distal bore 34 in the rotator head.

After a heart valve has been initially stitched into an appropriate location within the heart, the heart rotator of our invention can be used to orient the annular body of the heart valve within its sewing ring, thus orienting the leaflets. By bending the shaft 12, the surgeon can bring the rotator head into appropriate contact with the heart valve despite limitations imposed by the physiology of a patient or by the surgical techniques selected for implanting the valve. By turning the drive knob 18, the surgeon can then turn the annular body of the valve to any desired orientation.

Figure 5:
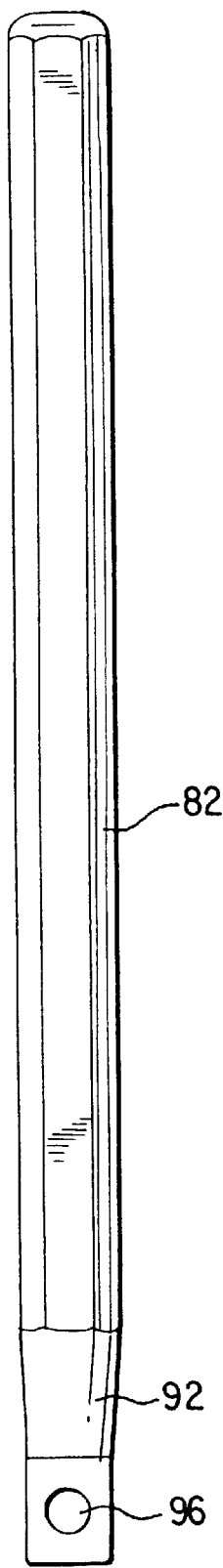
FIG. 5 is a plan view of a handle of the embodiment of FIG. 4.
Figure 7:
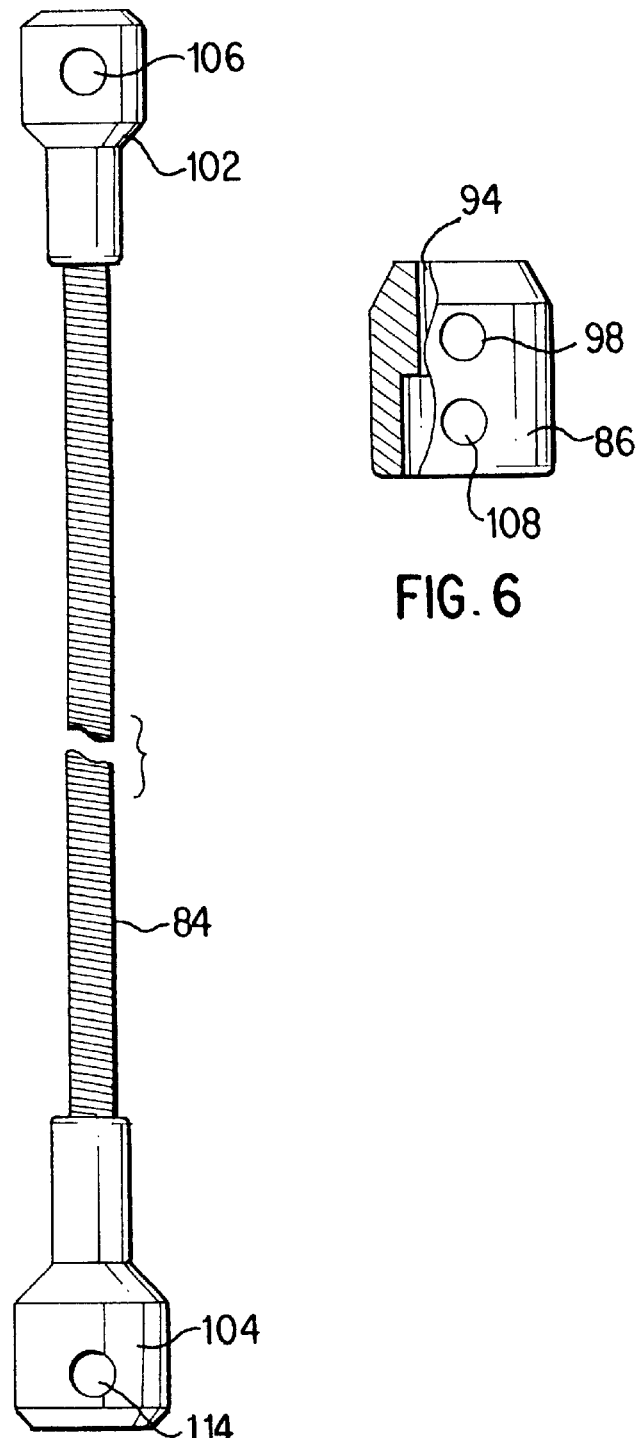
FIG. 7 is a plan view of a coil drive shaft of the embodiment of FIG. 4.
Figure 6:
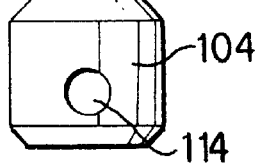
FIG. 6 is a plan view with partial through section of a distal connector from the embodiment of FIG. 4.

Referring now to FIGS. 4 through 12, a second embodiment of a heart valve rotator, generally designated 80, is illustrated. The heart valve rotator 80 comprises a handle 82 and a drive coil 84. A distal connector 86 fastens the handle 82 to the drive coil 84. A proximal connector 88 fastens the drive coil 84 to a removable rotator head 90. As illustrated in FIG. 5, the handle 82 is a generally linear rod, having, in our preferred embodiment, a hexagonal outline, with a proximal end 92 adapted to fit into a bore 94 in the distal connector 86. A through bore 96 in the proximal end 92 of the handle 82 matches a through bore 98 in the connector 86. A pin 100 is inserted through the bores 96, 98 to secure the handle and the distal connector 86. The drive coil 84 is a flexible stainless steel coil with a distal fitting 102 and a proximal fitting 104. Flexible coils of this type are commercially available, for example from S.S. White Technologies, Inc. A through bore 106 in the distal fitting 102 corresponds to a second through bore 108 in the distal connector 86. A second pin 110 is inserted through the bores 106,108 to secure the coil shaft 84 in the connector. Proximally, the proximal fitting 104 is adapted to fit in the proximal connector 88 in a cavity 112. A through bore 114 in the proximal connector 104 corresponds to a third through bore 116 in the proximal connector. A third pin 117 is inserted though the bores 114, 116 to secure the connector 88 to the fitting 104.

The rotator head 90 is of a type heretofore described in U.S. patent application Ser. No. 08/018,882 now U.S. Pat. No. 5,403,305, the disclosure of which is incorporated herein by reference. Preferably, the rotator head 90 is secured in the connector 88 by a D-ring 118 in a manner also described in the referenced patent. As shown in FIGS. 8 through 13, the connector 88 comprises a hexagonal distal cavity 120 adapted to receive a hexagonal post 122 on the rotator head 90. A circumferential groove 124 on the connector 88 receives the D-ring 118. The groove 124 cuts into the cavity 120 on one side of the connector 88 forming an opening 126 into the distal cavity 120. A flat segment 128 on the D-ring 118 protrudes through the opening 126 into the cavity 120 and engages a circumferential groove 130 on the post of the rotator head. The rotator head 90 is also provided with leaflet engaging surfaces 132, 134 which are adapted to abut the leaflets of a mechanical heart valve. In the embodiment shown, a bileaflet heart valve is contemplated, but it is to be understood that different configurations of the rotator head 90 could be selected depending on the type or configuration of the heart valve to be manipulated. In use, the flexible coil 84 permits the surgeon to rotate the heart valve despite otherwise confining conditions which may occur during surgery.

FIG. 13 illustrates another embodiment of our invention. The heart valve prosthesis rotator 140 is shown with handle 14 at the proximal end and rotator head 16 at the distal end. Of course, head 16 can be configured in a variety of ways, so long as it contains means for engaging the annular valve body of the heart valve prosthesis, and means for turning the rotator about center-line 3 of the shaft 142. Connecting the rotator head 16 and handle 14 is elastic shaft 142. Shaft 142 is constructed of a single piece of highly elastic material, preferably super-elastic form of nickel titanium (nitinol) alloy. "Super-elastic" refers to the unusual ability of certain metal to undergo large elastic deformation. This superelasticity in nitinol occurs only in a relatively narrow temperature range just above the austenite finish $(A_f)$ temperature. Shaft 142 provides both flexibility and torqueability to rotator 140.

Shaft 142 has the ability to absorb large amounts of strain energy and release it as the applied strain is removed. Thus, shaft 142 can be manipulated without plastic deformation, and at the same time maintain excellent torqueability, to rotate the prosthetic heart valve to the desired location. Not only does shaft 142 have the characteristics of flexing and rotating that exist in the other embodiments disclosed herein, but also, shaft 142 is less bulky and can manipulate a prosthetic valve in a very limited space. The ability to operate rotator 140 in a limited space is always important during cardiac surgery, but is particularly necessary when performing less-invasive (i.e., intracardiac procedures) surgery. Moreover, rotator 140 is more easily sterilized.

Figure 14A:
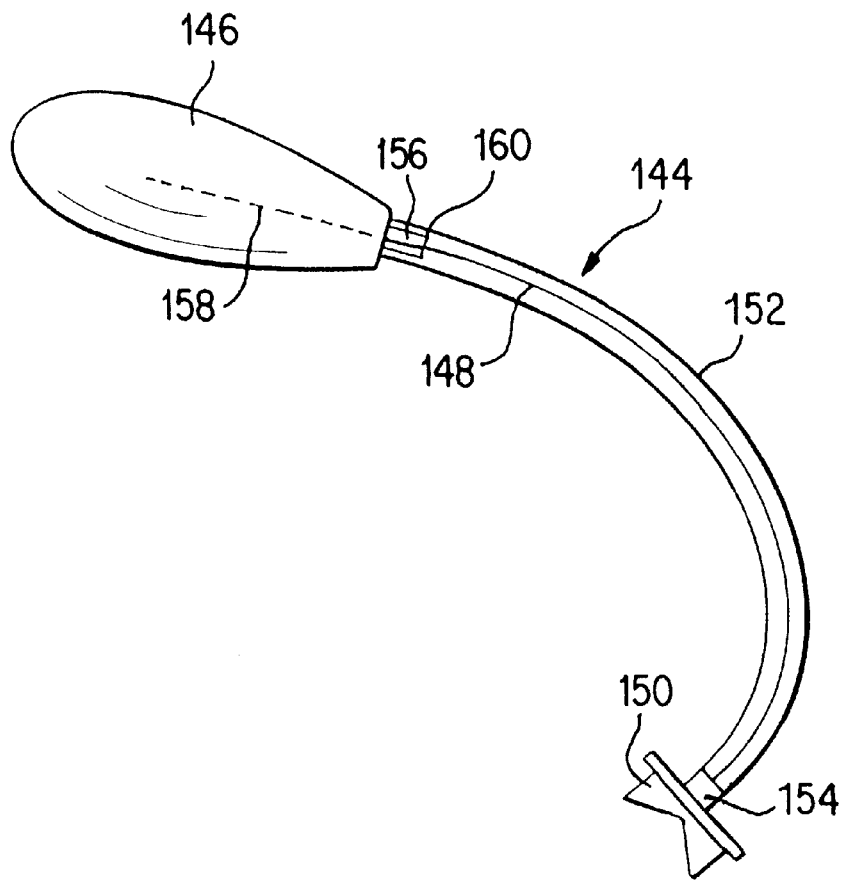
FIG. 14A is a plan view of a fourth embodiment of an invention.
Figure 14B:
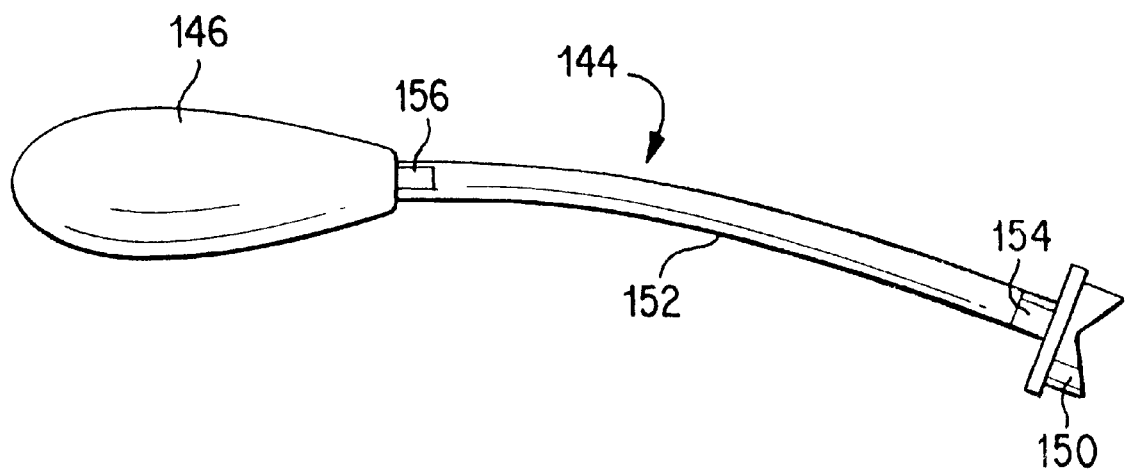
FIG. 14B is a plan view of a fifth embodiment of our invention

FIGS. 14A and 14B represent another embodiment of our invention. Referring to FIG. 14B, rotator 144 consists essentially of three components: rotator head 150, shaft 152, and handle 146. The head 150 and handle 146 may be constructed of plastic or other polymer, and can be fabricated by inexpensive mass-production means such as plastic injection molding. Head 150 and handle 146 have ferrules 154 and 156 respectively onto which shaft 152 can be attached. These ferrules 154, 156 are designed so that there is no slippage during rotation and so that all components remain attached. Shaft 152 is constructed of a section of surgical tubing (e.g. tygon tubing). The combination of head 150, shaft 152, and handle 146 creates a functional and inexpensive device that can be either reusable or disposable. The surgeons can cut the tubing of shaft 152 to shorten it, or can replace the tubing with a longer piece to lengthen shaft 152.

Another version of this embodiment is shown in FIG. 14A, which uses wire stiffening 148 to stiffen and shape shaft 152. The wire 148 is loosely mounted in the rotating head 150 and is inserted into axial hole 160 of handle 146. The wire 148 may extend into handle 146 to allow adjustment of shaft 152 length. By bending wire 148, a bent shaft 152 would result, about which head 150 and handle 146 will rotate. This feature provides additional positional control and stability to the rotator, and allows the surgeon to shape the device as desired before inserting it.

Our invention may be embodied in other specific forms without departing from the spirit or other essential characteristics thereof. The foregoing description is, therefore, to be viewed in all respects as illustrative and not restrictive. The scope of our invention is defined by the appended claims, and all variants within the scope of equivalency of the claims are intended to be included therein.

We claim as our invention:

1. A rotator for a mechanical heart valve comprising:
   a handle;
   a super-elastic shaft attached to said handle; and
   a rotator head adapted to engage an annular valve body within said mechanical heart valve.

2. The rotator of claim 1 wherein said super-elastic shaft comprises super-elastic nickel-titanium alloy.

3. The rotator according to claim 1 wherein said rotator head has an internal bore and said shaft has retainer means at said proximal end thereof for securing said rotator head, said retainer means being within said bore.

4. The rotator according to claim 1 further comprising connector means attached to a proximal end of said shaft for releasably connecting said rotator head to said shaft.

5. The rotator according to claim 1 wherein said rotator head further comprises at least one surface for engaging at least one leaflet in said mechanical heart valve.

6. A rotator for a mechanical heart valve comprising:
   a handle;
   a shaft attached to said handle, said shaft comprising a super-elastic, axially rotatable material and having a proximal end; and
   a head at said proximal end of said shaft for engaging an annular valve body within said mechanical heart valve.

7. The rotator according to claim 6 wherein the rotator is sterilizable.

8. The rotator of claim 6, wherein said super-elastic axially rotatable material is a nickel-titanium alloy.

* * * * *